United States Patent
Stewart et al.

(10) Patent No.: US 8,326,546 B2
(45) Date of Patent: Dec. 4, 2012

(54) METHODS AND APPARATUS FOR EVALUATING GLUCOSE LEVELS AROUND A REPEATING EVENT

(75) Inventors: Doshia Stewart, Indianapolis, IN (US); John R. Sullivan, Carmel, IN (US); Lisa N. Huse, Indianapolis, IN (US); William Polonsky, Encinitas, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 442 days.

(21) Appl. No.: 12/621,836

(22) Filed: Nov. 19, 2009

(65) Prior Publication Data

US 2011/0118986 A1    May 19, 2011

(51) Int. Cl.
*G06F 19/00*    (2011.01)
(52) U.S. Cl. .............. 702/19; 705/3; 600/365
(58) Field of Classification Search .......... 702/19, 702/179; 705/3; 604/66, 8, 93.1; 600/347, 600/309, 345, 365, 301, 37; 606/191
See application file for complete search history.

(56) References Cited

U.S. PATENT DOCUMENTS

| | | | |
|---|---|---|---|
| 5,437,024 A | | 7/1995 | French |
| 7,651,845 B2 * | | 1/2010 | Doyle et al. ............ 435/14 |
| 2005/0177397 A1 | | 8/2005 | Kane |
| 2006/0272652 A1 | | 12/2006 | Stocker et al. |
| 2007/0016449 A1 * | | 1/2007 | Cohen et al. ............ 705/3 |
| 2007/0033074 A1 | | 2/2007 | Nitzan |
| 2007/0055799 A1 | | 3/2007 | Koehler |
| 2009/0018779 A1 * | | 1/2009 | Cohen et al. ........... 702/19 |
| 2009/0030733 A1 * | | 1/2009 | Cohen et al. ............ 705/3 |
| 2009/0150186 A1 * | | 6/2009 | Cohen et al. ............ 705/3 |
| 2009/0271729 A1 | | 10/2009 | Clark et al. |
| 2010/0069730 A1 * | | 3/2010 | Bergstrom et al. ...... 600/365 |
| 2010/0218132 A1 * | | 8/2010 | Soni et al. ............ 715/771 |
| 2010/0262434 A1 * | | 10/2010 | Shaya .................. 705/3 |
| 2010/0292634 A1 * | | 11/2010 | Kircher et al. .......... 604/66 |
| 2012/0059673 A1 * | | 3/2012 | Cohen et al. ............ 705/3 |

FOREIGN PATENT DOCUMENTS

| | | |
|---|---|---|
| EP | 0 800 082 A2 | 10/1997 |
| WO | 2006/121548 A2 | 11/2006 |
| WO | 2009 106300 A1 | 9/2009 |

OTHER PUBLICATIONS

Accu-Chek Smart Pix User's Manual V 2 0 EN (90 pages), Feb. 2008.

* cited by examiner

*Primary Examiner* — Carol Tsai
(74) *Attorney, Agent, or Firm* — Dinsmore & Shohl LLP (57) ABSTRACT

Methods for evaluating changes in glucose levels include selecting a repeating event, obtaining a pre-event measurement and a post-event measurement for a plurality of occurrences of the repeating event wherein a glucose change between the pre-event measurement and post-event measurement may be determined for each of the plurality of occurrences of the repeating event, and, recording unique details for each of the plurality of occurrences of the repeating event such that the unique details may be correlated with the glucose change for each of the plurality of occurrences of the repeating event.

23 Claims, 4 Drawing Sheets

METHODS AND APPARATUS FOR EVALUATING GLUCOSE LEVELS AROUND A REPEATING EVENT

TECHNICAL FIELD

The present disclosure generally relates to monitoring diabetes, and, in particular, to methods and devices for monitoring glucose levels around a selected repeating event.

BACKGROUND

For people with diabetes, successful management requires monitoring the effects lifestyle changes can have in both short-term and long-term time frames. Regular testing of their blood glucose level can be an important part of diabetes management as a way to track changes throughout the day. For example, portable handheld medical diagnostic devices are often employed to measure concentrations of biologically significant components of bodily fluids, such as, for example, glucose concentration in blood. To test glucose with a glucose meter, a small sample of blood may be placed on a disposable test strip. The portable handheld glucose meter may include a strip port that receives the disposable test strip. The test strip may be coated with chemicals (glucose oxidase, dehydrogenase, or hexokinase) that combine with glucose in blood allowing it to measure the concentration of glucose in the blood sample. The portable handheld glucose meter then displays the glucose concentration as a number (or glucose measurement value). As a result, the portable handheld medical diagnostic devices and their accessories may work together to measure the amount of glucose in blood and be used to monitor glucose levels in one's home, healthcare facility or other location, for example, by persons having diabetes or by a healthcare professional.

Patients and healthcare professionals may thereby track and analyze glucose measurements over a period of time to asses changes in the patient over the course of a day, week or other desirable timeframe. For example, some healthcare professionals may instruct a patient to obtain glucose measurements seven or more times a day over a course of a few consecutive days so that patients may observe the changes their measurements undertake. However, such repetitious testing may be tedious for a patient and difficult to maintain. Furthermore, the significance in changing lifestyle factors (such as meal portions or physical activity) may not always be immediately noticeable to all patients. While patients with Type 1 or Type 2 diabetes who have progressed to full insulin dependence may immediately notice the consequences of missed glucose testing and/or insulin dosing, patients not dependent on insulin largely work towards long term benefits that may be difficult to appreciate in the short term. As such, patients seeking immediate rewards may lack motivation to effectively monitor their diabetes or embrace beneficial changes to their daily routines. Thus it may be desirable to provide alternative methods and apparatuses for monitoring glucose levels through concentrating testing around a specific event to allow for a simpler assessment of how small changes can influence their physical condition.

SUMMARY

In one embodiment, a method for evaluating changes in glucose levels is provided. The method includes selecting a repeating event, obtaining a pre-event measurement and a post-event measurement for a plurality of occurrences of the repeating event wherein a glucose change between the pre-event measurement and post-event measurement may be determined for each of the plurality of occurrences of the repeating event, and, recording unique details for each of the plurality of occurrences of the repeating event such that the unique details may be correlated with the glucose change for each of the plurality of occurrences of the repeating event.

In another embodiment, a method is provided for evaluating changes in glucose levels through variations on a repeating event. The method includes selecting a repeating event, selecting variations on the repeating event such that unique details are recorded for each occurrence of the repeating event, and, obtaining a pre-event glucose measurement and a post-event glucose measurement for each occurrence of the repeating event such that a glucose change may be correlated with the unique details of each occurrence of the repeating event.

In yet another embodiment, an electronic device is provided for evaluating changes in glucose levels around an event. The electronic device includes a display, an input terminal for inputting pre-event measurements, post-event measurements and unique details for a plurality of occurrences of a repeating event, memory for storing the pre-event measurements, post-event measurements, unique details and instructions, and, a processor in communication with the memory and operable to execute the instructions, the instructions causing the processor to determine a glucose change between the pre-event measurement and post-event measurement for each of the plurality of occurrences of the repeating event such that the glucose change may be correlated with the unique details for each of the plurality of occurrences of the repeating event.

In still yet another embodiment, a glucose change evaluation chart is provided. The glucose change evaluation chart includes a pre-event column, a post-event column and a change column, and a plurality of rows associated with the pre-event column, post-event column and change column for respectively recording a pre-event measurement, a post-event measurement and a glucose change between the pre-event measurement and post-event measurement for each of a plurality of occurrences of a repeating event. The glucose change evaluation chart further includes a unique details area adjacent the change column for recording unique details for each of the plurality of occurrences of the repeating event such that the unique details are correlated with the glucose change for each of the plurality of occurrences of the repeating event.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which.

DETAILED DESCRIPTION

Embodiments of the present disclosure are directed to monitoring diabetes, and more specifically to monitoring the effect changes in a repeating event may have on the changes in glucose levels caused by the event. Patients with diabetes may select a repeating event, take a pre-event and post-event measurement for each occurrence of the repeating event and record the unique details (or variations) for each occurrence of the repeating event such that the unique details of each occurrence of the repeating event may be compared to the different changes in glucose levels. This may allow for a patient, health care provider or any other party to see the influence small lifestyle changes may have with respect to changes in glucose levels.

It is to be appreciated that in addition to the above noted benefits the embodiments of the present invention also enable self-discovery by the patient with diabetes. Self-discovery can accelerate learning by making concepts tangible and relevant to the patient. For example, by focusing on one specific event or activity, the patient is involved and has ownership in investigating what contributes to blood glucose (bG) spikes related to that specific event or activity. By focusing on one specific event or activity at a time, the patient may not be overwhelmed and the impact of a specific lifestyle choice on overall bG control can be isolated. In this manner, the patient can discover if a prescribed regimen works and determine for themselves whether a change in behavior is worthwhile. For example, patients with type 1 diabetes can use paired testing to understand how their body responds to different behaviors, like exercise, change in environment (e.g., going to camp, college, or work) or a change in routine (e.g., transition from a structured situation to the flexibility of holidays). Patients with type 2 diabetes are often asked to change multiple behaviors at once from food choices, portion sizes, exercise, etc., but the health impact is not always seen immediately. Paired testing links lifestyle to bG levels and thus reduces skepticism that a prescribed regime is worthwhile. Additionally, if the patient is receiving diabetes education, such as those with gestational diabetes, using the present invention to weave paired testing activates or events as explained hereafter into an education curriculum can help reinforce learning at each step and help link bG variation to daily lifestyle choices.

Figure 1:
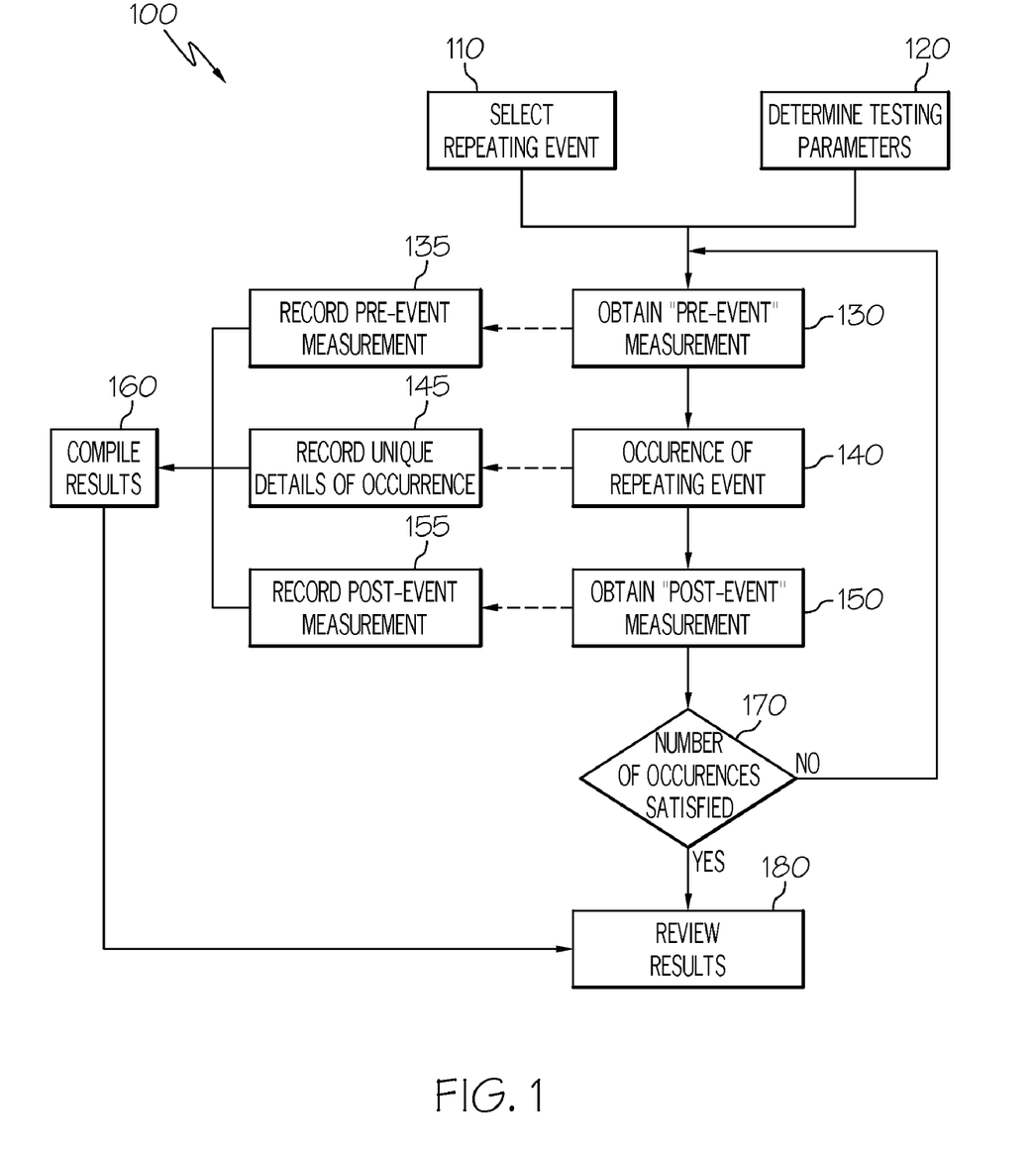
FIG. 1 depicts a logistical flowchart for evaluating glucose measurements around a repeating event according to one or more embodiments shown or described herein.

Referring to FIG. 1, an exemplary method 100 is depicted for monitoring changes in glucose levels around a repeating event. A patient and/or healthcare provider may first select a repeating event in step 110 for the monitoring of glucose levels in the blood, or any other similarly related measurement for monitoring diabetes. Repeating events may comprise any repetitious act or event that a patient may undergo or perform. For example, repeating events may include general acts of eating, a specific meal (such as breakfast, lunch or dinner), general acts of physical activity, a specific type of physical activity (such as jogging, swimming or walking) or any other event that is repeated over a period of time. Repeating events may repeat throughout a single day, repeat every day or may otherwise repeat over non-consecutive days or over some other time frame. Repeating events may further repeat any number of times that allows for a patient and/or healthcare provider to compare changes in glucose levels with the unique details of each occurrence of the repeating event as should become appreciated herein. In addition, repeating events may be subject to variations such that unique details may be recorded for each occurrence of the repeating event as should also become appreciated herein.

The selection of a repeating event in step 110 may be performed by a patient, healthcare provider or any other party or combinations thereof. Furthermore, the repeating event may be selected to obtain a general assessment of the patient, to target specific problems reported by the patient or otherwise be based on the ease of completion by the patient. The repeating event may also be selected based on self-interest in knowing more about the effect of an activity or event on bG control or based on an indication provided from another tool such as, for example, ACCU-CHEK 360° View tool, ACCU-CHEK Smart Pix device, or ACCU-CHEK 360° software (all from Roche Diagnostics), as an area of interest. For example, where a patient is relatively inexperienced with diabetes management or lacks an appreciation on how meal portions create changes in glucose levels, the repeating event may comprise the meal (e.g. breakfast, lunch or dinner) the patient most regularly eats to study the effect that variations on that meal may have on their glucose levels. In another example, the patient may express concern on what types of food she should or should not eat. In such an example, the repeating event may comprise a meal where the patient varies foods so that the patient may ultimately be able to see the different changes in glucose levels caused by the different foods the patient consumes. In yet another example, the patient may report a recent change in their overall health that may be caused by a recent change in their lifestyle (such as walking less or eating more). The repeating event selected in step 110 may thereby comprise the identified change in lifestyle so that the change can be monitored to see whether it may be partly responsible for their change in health. Selecting a repeating event in step 110 may alternatively comprise any repeating event selected by any party through any analysis such that a specified event that repeats is ultimately determined for the monitoring of changes in glucose levels, or other diabetes related measurements, around said event.

Still referring to method 100 in FIG. 1, additional testing parameters may further be determined in step 120. Determining testing parameters may comprise determining the number of occurrences of the repeating event to test around, the time period before or after each occurrence of the repeating event to test for, or planned variations on the repeating event such that those planned variations may be monitored. For example, the number of occurrences of the repeating event may depend in part on the motivation of the patient or the type of repeating event selected in step 110. In one embodiment, the number of occurrences of the repeating event to test around may be no fewer than three. In another embodiment, the number of occurrences of the repeating event may be seven such that the patient may obtain measurements for every day of the week for one week. In yet another embodiment, the number of occurrences may not be specifically defined but rather the patient may test around a repeating event every time the repeating event occurs over some defined period of time. For example, the patient may obtain measurements before and after exercising every time they exercise up until their next doctor's appointment.

Determining testing parameters in step 120 may further comprise defining when to obtain a pre-event measurement and/or a post-event measurement with respect to the occurrence of the event. Such a determination may depend on the type of repeating event selected in step 110. For example, in one embodiment, the pre-event measurement may be obtained immediately before the occurrence of the repeating event such as immediately before the patient begins eating or immediately before the patient begins exercising Likewise, the post-event measurement may be obtained either immediately after the occurrence of a repeating event (such as immediately after exercise) or for some specified time period after the commencement or conclusion of an event (such as two hours after taking the first bite of food or after finishing the meal). The determination of testing parameters in step 120 may further comprise selecting planned variations on the repeating event such that those planned variations may specifically be examined with respect to changes in glucose levels. For example, the patient and/or healthcare provider may decide to vary meal sizes or the amount of physical activity to monitor any changes brought about by such variations. Determining testing parameters in step 120 may further comprise any other determinations which may influence the monitoring of diabetes such as which type of measurement to obtain, how to obtain measurements or how to record measurements. Furthermore, determining the testing parameters in step 120 may occur before, after or simultaneous with selecting a repeating event in step 110 and may also influence or be influenced by the selection of a repeating event in step 110.

After the repeating event and testing parameters have been selected in steps 110 and 120, the patient may obtain measurements around a plurality of occurrences of the repeating event. Specifically, the patient may obtain a pre-event measurement and a post-event measurement for each occurrence of the repeating event. Referring to method 100, for every occurrence of the repeating event in step 140, the patient may obtain a pre-event measurement in step 130 before the occurrence of the repeating event, and obtain a post-event measurement in step 150 sometime after the occurrence of the repeating event. As discussed above, the time between steps 130, 140 and 150 may be influenced by the testing parameters determined in step 120 and/or the type of event selected in step 110. The measurements may comprise any diabetes related measurement such as the glucose level in the patient's blood. In addition, the measurement may be obtained through any of the various testing means available such as through portable glucose monitors or alternative methods. In one embodiment, the patient may obtain a sample of blood to obtain the measurement at a specific time before and/or after the event occurs. In another embodiment, where a continuous blood glucose meter continuously monitors glucose levels in the patient, the patient may enter the occurrence of the repeating event into the continuous blood glucose meter such that the pre-event measurement and post-event measurement are automatically obtained by the continuous blood glucose meter.

In addition to obtaining a pre-event measurement and post-event measurement for each occurrence of the repeating event, the patient may obtain unique details for each individual occurrence of the repeating event. Unique details may comprise the details relevant to that specific occurrence of the event such as any variations that particular occurrence might have experienced with respect to other occurrences of the repeating event. Unique details may, for example, include types of meals, meal portions, types of exercise, amount of exercise, intensity of exercise, or whether physical activity was combined with or followed a meal. Unique details may further or otherwise include any other information specific to a single occurrence of the repeating event that may be applicable to evaluating the glucose changes around the occurrence of the repeating event by the patient, healthcare provider or any other party. For example, where the patient selected a meal as the repeating event in step 110 to evaluate which foods she should or should not eat, the unique details for each occurrence of the repeating event in step 140 may comprise the type of food she consumed for each meal. Likewise, where the patient selected dinner as the repeating event in step 110 to analyze the effects of incorporating physical activity into their dinner, the unique details for each occurrence of the repeating event in step 140 may comprise whether the patient walked after the meal, and if so, how long she walked for. In another embodiment, the unique details for each occurrence of the event may comprise all information specific to each occurrence of the repeating event such that the patient and/or health care provider may examine for trends after the completion of method 100 without having a predetermined strategy on which variations to examine in terms of changes in glucose levels as should be appreciated herein. It should be noted that the above examples are illustrative only and by no means meant to be limiting on what information can comprise the unique details for each occurrence of the repeating event.

The information obtained from each occurrence of the repeating event is subsequently recorded in steps 135, 145 and 155. The recordation of each individual entry (i.e., pre-event measurement in step 135, unique details in step 145 and post-event measurement in step 155) may occur directly after each correlated step is completed (i.e. steps 130, 140 and 150), may be delayed such that all entries can be entered at the same time directly before a party reviews the results in step 180, or may occur in any other chronological order with respect to steps 130, 140 and 150. Furthermore, the pre-event measurement, unique details and post-event measurement may be recorded manually or automatically and may be recorded by hand or electronically. The obtaining of a pre-event measurement in step 130 and a post-event measurement in step 150 for each occurrence of the repeating event in step 140 may then continue until the number of occurrences of the repeating event has been satisfied as indicated in step 170. For example, if the patient and/or healthcare provider determined that the patient will obtain said measurements around each dinner for one week, the method will repeat until the patient has obtained measurements and unique details for seven occurrences of the repeating event. As discussed above, the satisfaction of the number of occurrences of the repeating event in step 170 can be realized due to the specific number of occurrences of the repeating event, or can be realized by the exhaustion of an overall time period in which the repeating event may occur.

The method of obtaining pre-event and post-event measurements (as well as unique details about the specific occurrence of the event) may then be compiled in step 160 before the results are reviewed in step 180. Compiling the results in step 160 may comprise determining the glucose change for each occurrence of the repeating event (i.e. the difference between the pre-event measurement obtained in step 130 and the post-event measurement obtained in step 150) and correlating the glucose change for each occurrence with its corresponding unique details. Correlating the glucose change with the unique details of each occurrence of the repeating event may thereby allow the patient and/or healthcare provider to examine the different glucose changes brought on by the different unique details (or the variations on the repeating event). Without intending to be bound by a particular theory, such examination may allow for an appreciation by the patient on how variations (such as smaller food portions, healthier food options or increased physical activity) on the repeating event can affect their diabetes and may thereby promote beneficial changes to their lifestyles.

Figure 2:
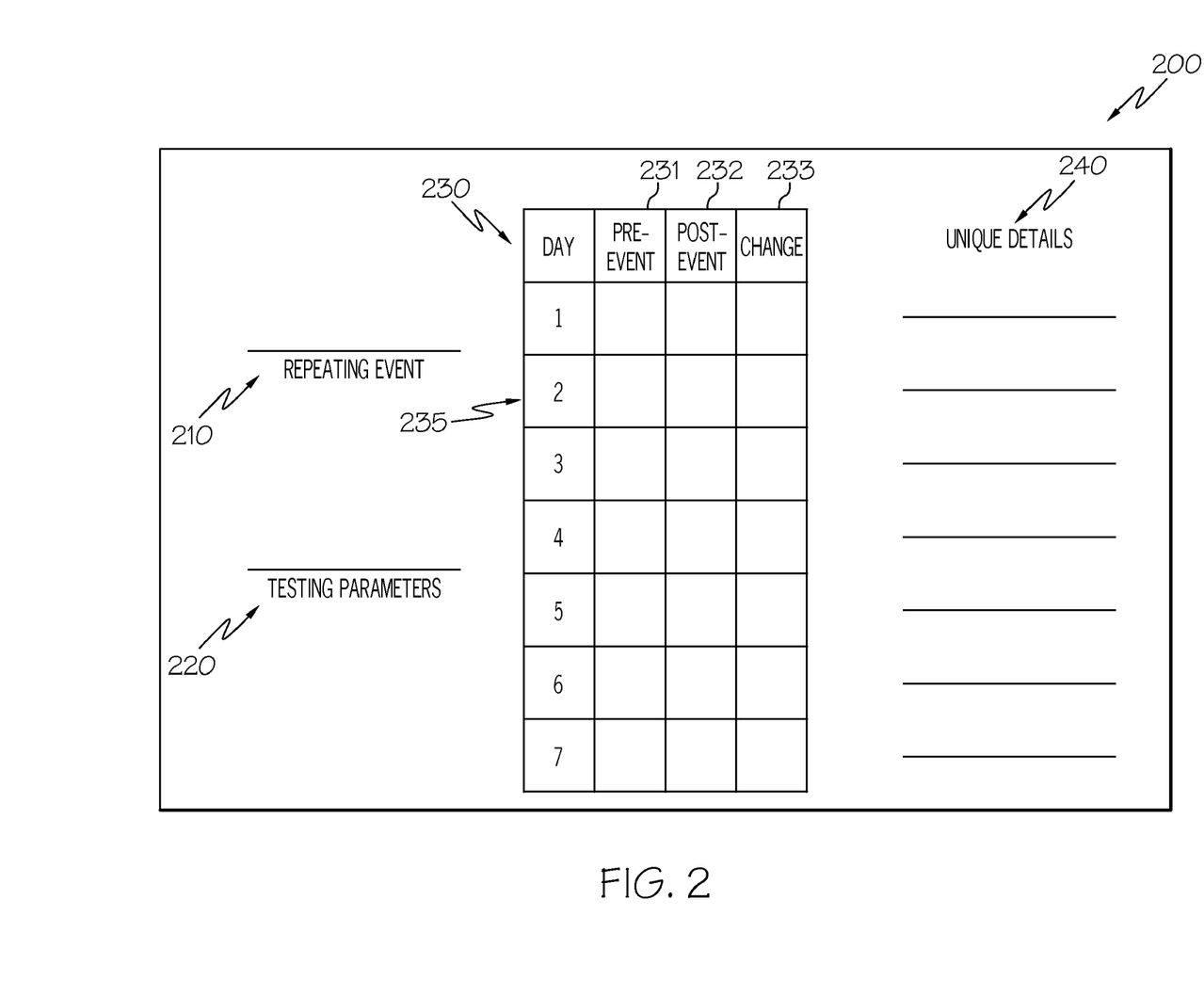
FIG. 2 depicts an exemplary chart for evaluating glucose measurements around a repeating event according to one or more embodiments shown or described herein.

Referring now to FIG. 2, an exemplary glucose change evaluation chart 200 for compiling and reviewing results (as performed in steps 160 and 180 in the method 100 of FIG. 1)

is illustrated. The glucose change evaluation chart 200 may comprise a "Repeating Event" area 210 where the repeating event may be written and a "Testing Parameters" area 220 where any relevant or noteworthy parameters (such as how long to wait after an occurrence before obtaining a post-event measurement) may be written. The glucose change evaluation chart 200 may further comprise a measurements section 230 comprising a plurality of columns 231,232,233 and a plurality of rows 235 for the recordation and reference of the pre-event measurements, post-event measurements and glucose changes there between. Specifically, the glucose change evaluation chart 200 may comprise a pre-event column 231, a post-event column 232 and a change column 233. A plurality of rows 235 can be associated with the pre-event column 231, post-event column 232 and change column 233 for respectively recording a pre-event measurement, a post-event measurement and a glucose change between the pre-event measurement and post-event measurement for each of a plurality of occurrences of a repeating event. Additionally, the chart 200 may comprise a unique details area 240 where a patient may record the unique details for each occurrence of the repeating event. The unique details area 240 may be adjacent the change column 233 such that the unique details may be correlated with the glucose change for each of the plurality of occurrences of the repeating event. A patient may therefore, for example, be able to quickly reference how a larger meal or less physical activity results in a higher change between there pre-event and post-event measurements or how engaging in physical activity following a meal limits the glucose change caused by the meal. The glucose change evaluation chart 200 may alternatively include any other information that may be beneficial to the patient or health care provider such as general instructions, testing dates or contact information for the healthcare provider.

Figure 3:
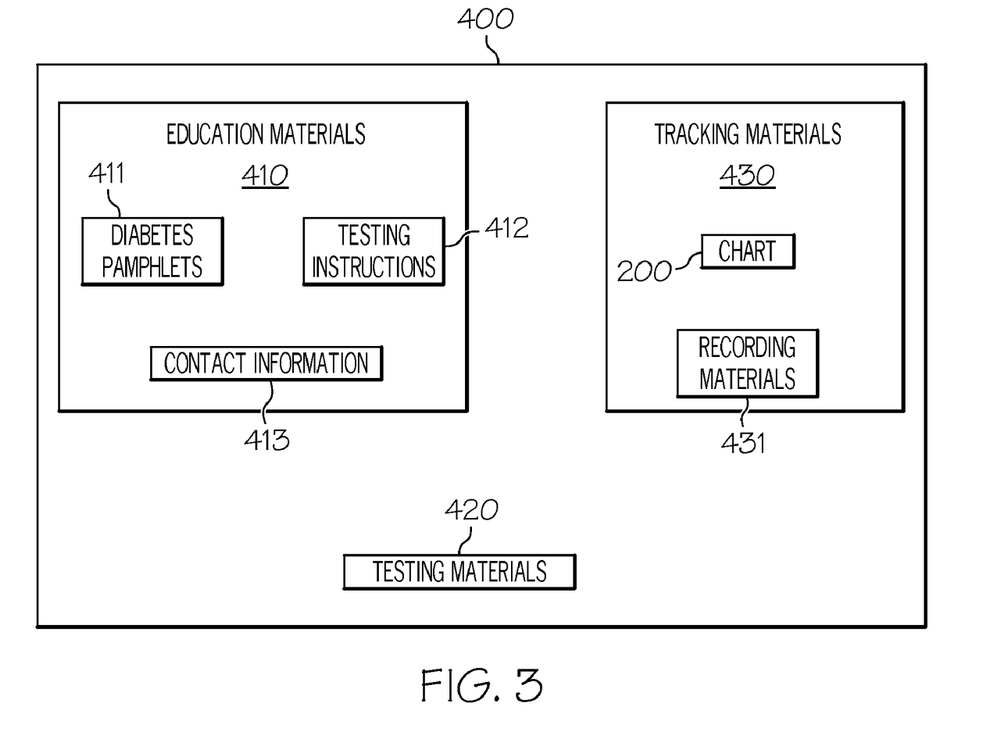
FIG. 3 depicts an exemplary glucose change evaluation chart according to one or more embodiments shown or described herein, and, FIG. 4 depicts an exemplary electronic device for evaluating glucose measurements around a repeating event according to one or more embodiments shown or described herein.

The glucose change evaluation chart 200 may be incorporated as a stand-alone form, e.g. pre-printed on a sheet of paper, as part of a log book for tracking other diabetes related information, as part of a pamphlet introducing patients to dealing with diabetes or in any form that would allow for a patient, healthcare provider or other party to evaluate glucose changes around individual occurrences of repeating events. For example, referring now to FIG. 3, in one embodiment the glucose change evaluation chart 200 may be provided as part of a diabetes management package 400. The diabetes management package may comprise a plurality of elements such as education materials 410, testing materials 420 and tracking materials 430. The education materials 410 may comprise items such as diabetes pamphlets 411, testing instructions 412 or contact information 413 that may educate a user in diabetes management and provide an appreciation for how to use the contents of the diabetes management package 400. The diabetes management package 400 may further comprise testing materials 420. Testing materials can comprise any materials or devices operable to obtain diabetes related measurements such as glucose levels. For the example, in one embodiment, testing materials 420 can comprise an electronic device such as a blood glucose meter. The package can also comprise tracking materials 430 such as a glucose change evaluation chart 200 and additional recording materials 431 such as writing utensils or reminder alarms.

Figure 4:
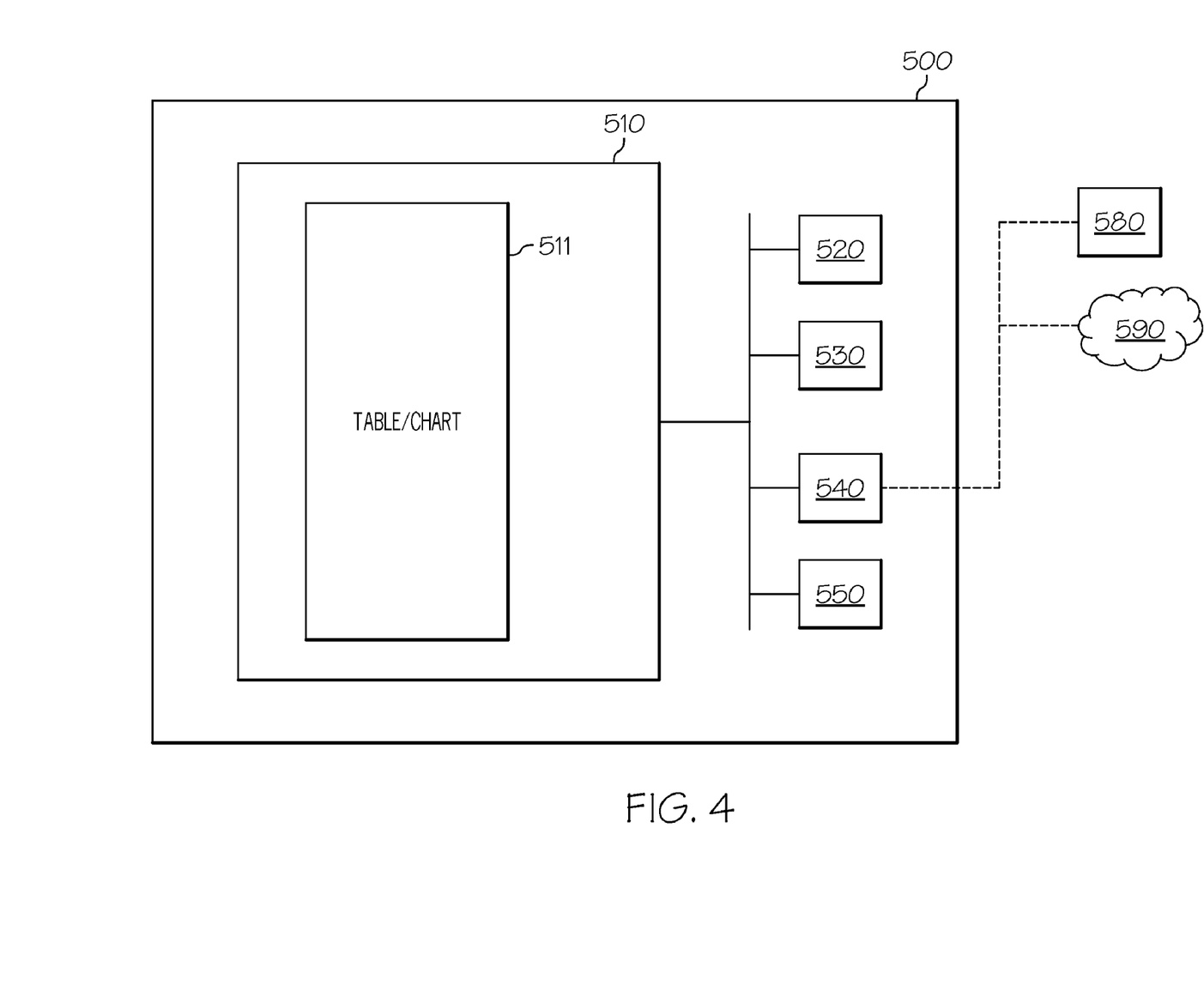

In another embodiment, referring now to FIG. 4, an electronic device 500 may obtain, store, compile and/or display the pre-event and post-event measurements and unique details for each occurrence of the repeating event. For example, in one embodiment, the electronic device 500 may comprise a display 510 for showing a table 511 or other obtained information as discussed above. The display 510 may, for example, show the glucose change evaluation chart 200 as table 511 with the pre-event measurement, post-event measurement, changes between the two measurements as well as the unique details for each occurrence of the repeating event. The electronic device 500 may further comprise a processor 520, memory 530, and one or more input terminals 540, 550. The processor 520 may process information such as computing changes between pre-event and post-event glucose measurements or determining whether the number of occurrences of the repeating event has been satisfied. The memory 530 may be operable to store the programs mentioned earlier and in sections hereafter, program instructions which cause the processor 520 to perform the steps of method 100, and information such as measurements, unique details, testing parameters or operator preferences. The input terminal 550 may comprise any mechanism for inputting data, operator feedback or other information for routine handling by the processor of the device. For example, in one embodiment the device 500 may comprise an input terminal for receiving glucose information and another input terminal (such as a keyboard or a touch screen) for operator communication of unique details. In addition, examples of routine handling may include the processor 520 storing input received via the input terminal 550 into the memory 530, retrieving information from the memory 530 based on input received via the input terminal 550, like a request to display the compiled results of a completed.

For example, a user may select the repeating event (illustrated as step 110 in FIG. 1) and determine the testing parameters (illustrated as step 120 in FIG. 1) and enter such selections into the electronic device 500 via the input terminal 550. In table 511, the areas 210 and 220 may be displayed electronically on the display 510 for the purpose of showing such entered information. It is to be appreciated that areas 210 and 220 may also be drop down boxes providing a menu of selectable repeating events and testing parameters, respectively. The pre-event and post-event measurements may then be obtained manually by the user or automatically by the electronic device 500. For example, in one embodiment, the user may manually test their blood (steps 130 and 150 in FIG. 1), such as with test strips and a separate glucose meter, and enter the resulting measurements (steps 135 and 155 in FIG. 1) into the electronic device 500 via the input terminal 550. In yet another embodiment, such as where the electronic device 500 comprises a blood glucose meter implemented with the method 100 and chart 200, the electronic device may automatically obtain the pre-event and post-event measurements (steps 130 and 150 in FIG. 1) and record them to the memory 530. For example, the processor 520 can instruct the electronic device 500 to obtain and record measurements (steps 130, 135, 150 and 155 in FIG. 1) around the time the event is either known to occur or when the user inputs via the input terminal 550 that the event is occurring. In such embodiments, the entered/recorded pre-event and post-event measurements are then displayed on the display 510 in columns 231 and 232, respectively, as well as the computed change in 233 of glucose change evaluation chart 200 provided by table 511. The user of the electronic device 500 may then record in memory 530 the unique details (step 145 in FIG. 1) via the input terminal 550 and the processor 520 can compile the results (step 160 in FIG. 1) and show such results in area 240 that is provided by table 511 on display 510. In one embodiment, specific meals, portion sizes, medications, dosages, and/or exercises may also be provided as a drop down menu provided on display 510 for entry into area 240. In such an embodiment, protein and carbohydrate content can be automatically calculated by the processor 520 after user selection, and recorded in memory 530 and displayed with such selected information in area 240 on display 510. The determination of whether the number of occurrences has been satisfied (step 170 in FIG. 1) can be performed manually by the user or automatically by the processor 520 in the electronic device 500. Finally, the user may review the results (step 180 in FIG. 1) at any time either via the display 510 of the electronic device 500 or by printing or otherwise obtaining the compiled results from the electronic device 500.

In another embodiment, the electronic device 500 may be part of an information system, such as, for example, where a server 580 provides instructions and stores information such as the pre-event and post-event measurements and/or the unique details for each occurrence of the repeating event. In such an embodiment, the server 580 may communicate either directly or over a network 590, e.g., LAN, WAN, Internet, and the like, with the electronic device 500 via communications hardware 540 enabling wired and/or wireless communications therewith. In this manner, the complied results from any test may be downloaded or sent to a healthcare provider and/or another software tool for adding notes and/or to allow further evaluations and recommendations. For example, in one embodiment, the software tool may send back over the network 590 to the electronic device 500 coaching tips for meals and exercises changes/additions that are based on the complied results, which the patient can use. Other coaching tips may be physical changes to keep the patient engaged in the self-discover process, or other changes such prescribed changes from the HCP to medication, dosages, meals, portion sizes, testing parameters, and the likes. As the communication hardware 540, server 580, and network 590 are conventional and well understood by those skilled in the art, no further discussion is provided.

In one particular embodiment, the processor 520 is in communication with the memory 530 (and/or server 580) and operable to execute instructions stored therein. The instructions when executed by the processor 520 cause the processor to compile the obtained pre-event measurement, post-event measurement and unique details for each occurrence of the repeating event which can include determining the glucose change for each occurrence of the repeating event by calculating the difference between the pre-event measurement and post-event measurement for each occurrence of the repeating event.

In other embodiments, the electronic device 500 may be, but not be limited to, a blood glucose meter, a personal digital assistant (PDAs), a cell phone, a smart phone, an electronic logbook or any other computing device such as a laptop, a desktop or web-based computing platform. In still another embodiment, the display 510 may be accessed through a program capable of being installed on or accessed by various computers, hand held devices or the like. Furthermore, the display 510 may comprise a full color screen, a black and white screen, a monochromatic screen or any other color variation. The display 510 may comprise a liquid crystal display (LCD), a plasma display, a cathode ray tube (CRT), a projection display or any alternative technology operable to display glucose changes and unique details for a patient and/or healthcare provider.

To help illustrate the above benefits provided by the embodiments of the present invention, the following use case example is provided. In this use case example, the patient selects a question that can be answered with bG measurements, such as for example, "are certain breakfast foods impacting bG levels?" Using the glucose change evaluation chart 200 that has either been implemented electronically on electronic device 500 or non-electronically, such as a pre-printed form, the patient then tracks pre-event ("before") and post-event ("after") bG measurements around a particular activity or event 2 times a day for 7 days by recording and displaying such readings in the pre-event and post-event columns 231, 232. The repeating event is recorded and displayed in area 210 as well as any testing parameters in area 220 such as, for example, the date, when a "before" measurement should be taken, and the time increment that should occur between the "before" and "after" measurements. The patient also records and displays any unique details concerning the event for each day in area 240. Such unique details in this example may include portions and specific food choices made. The change between the "before" and "after" bG measurements are recorded or computed and displayed in column 233. In this example, after four days a pattern is noted that the "before" bG measurements are in a normal range, but that the "after" bG measurements are above the normal range and the difference between the two measurements are also above a recommend limit (e.g., no greater than a 50 point difference). The patient at this point decides to see if small changes can help, such as, for example, adding more protein or cutting portion sizes of high-carbohydrates items. In this example, the effect of the small changes is immediately apparent the next day results improve with both bG measurements being normal and the difference being below 50 points. Such improved results continue for the remaining days in the test. The improved results can be highlighted for easy reference. With the test completed, the patient now has a better understanding of the dynamics of their disease, thereby helping self-discovery and permitting reinforcement of self-discovery via a follow-up conversation with their health care provider. The health care provider can further provide additional observations noted in the information provided in the glucose change evaluation chart 200 and help both patient and health care provider form other ideas or areas of discovery in which to learn the particulars of the patient's disease.

It should now be understood glucose changes around the occurrences of repeating events may be correlated with unique details of each occurrence to evaluate the different glucose changes caused by variations on the repeating event. For example, the embodiments of the present invention are useful to explore at least food self-care recommendations, exercise self-care recommendation, or to confirm whether an earlier change, such as in medication type and/or dosage is working. In exploring food self-care recommendation, the embodiments of the present invention can help a patient to know, for example, how portion size or a food choice impacts bG spikes at a particular meal, to know the link between low energy levels and post-meal bG levels, to know how bG levels differ on weekends versus weekdays, to know whether after-meal bG levels on holidays or while traveling differ, to know whether adjusting an evening meal can lower fasting morning values, to know if a bedtime snack will bring a fasting morning values back to normal if low, and the likes. In exploring exercise self-care recommendation, the embodiments of the present invention can help a patient to know, for example, whether exercise will lower bG levels, to know whether one type of exercise lowers bG more effectively than another, and the likes. In confirming if an earlier change is working, the embodiments of the present invention can help a patient to know, for example, how a medication change impacts a post-meal bG control, to know whether a new medication improves morning fasting bG levels, to know how exercise affects bG control now that medication has changed, to whether a food choice is working, to know whether selected food portions are working, and the likes.

The above description and drawings are only to be considered illustrative of exemplary embodiments, which achieve the features and advantages of the present invention. Modification and substitutions to specific process steps, system, and setup can be made without departing from the spirit and scope of the present invention. For example, although a specific arrangement to the evaluation chart 200 has been presented by example, the information thereon may be presented in other format arrangements different from areas, column, and rows. Accordingly, the invention is not to be considered as being limited by the foregoing description and drawings, but is only limited by the scope of the appended claims.

What is claimed is:

1. A method for evaluating changes in glucose levels, the method comprising:
   selecting a repeating event;
   obtaining a pre-event measurement and a post-event measurement for a plurality of occurrences of the repeating event;
   determining a glucose change between the pre-event measurement and post-event measurement for each of the plurality of occurrences of the repeating event; and
   recording unique details for each of the plurality of occurrences of the repeating event such that the unique details are correlated with the glucose change for each of the plurality of occurrences of the repeating event.

2. The method of claim 1 wherein the repeating event comprises a meal.

3. The method of claim 2 wherein unique details comprise meal portions.

4. The method of claim 2 wherein unique details comprise types of food.

5. The method of claim 1 wherein the repeating event comprises physical activity.

6. The method of claim 5 wherein unique details comprise an amount of physical activity.

7. The method of claim 1 wherein the plurality of occurrences of the repeating event comprises between three and fourteen occurrences of the repeating event.

8. The method of claim 7 wherein the plurality of occurrences of the repeating event comprises seven occurrences of the repeating event.

9. The method of claim 1 wherein the method further comprises determining testing parameters.

10. The method of claim 9 wherein testing parameters comprise variations on the repeating event.

11. A method for evaluating changes in glucose levels through variations on a repeating event, the method comprising:
    selecting a repeating event;
    selecting variations on the repeating event;
    obtaining a pre-event glucose measurement and a post-event glucose measurement for each occurrence of the repeating event;
    determining a glucose change between the pre-event measurement and post-event measurement for each occurrence of the repeating event; and
    recording unique details of each occurrence of the repeating event, wherein the unique details are recorded based on the selected variations, such that the glucose change are correlated with the unique details of each occurrence of the repeating event.

12. The method of claim 11 wherein the repeating event comprises a meal.

13. The method of claim 12 wherein variations comprise changes in meal portions.

14. The method of claim 12 wherein variations comprise engaging in a physical activity following the meal.

15. The method of claim 11 wherein the repeating event comprises a physical activity.

16. The method of claim 15 wherein the variations comprise changes in amount of physical activity.

17. An electronic device for evaluating changes in glucose levels around an event, the electronic device comprising:
    a display;
    an input terminal for inputting pre-event measurements, post-event measurements and unique details for a plurality of occurrences of a repeating event;
    memory for storing the pre-event measurements, post-event measurements, unique details and instructions; and
    a processor in communication with the memory and operable to execute the instructions, the instructions causing the processor to determine a glucose change between the pre-event measurement and post-event measurement for each of the plurality of occurrences of the repeating event such that the glucose change are correlated with the unique details for each of the plurality of occurrences of the repeating event.

18. The electronic device of claim 17 wherein the electronic device comprises a blood glucose meter.

19. The electronic device of claim 18 wherein the electronic device comprises a continuous blood glucose meter operable for a patient to input occurrences of the repeating event such that pre-measurements and post-measurements are automatically obtained by the continuous blood glucose meter.

20. A glucose change evaluation chart comprising:
    a pre-event column, a post-event column and a change column;
    a plurality of rows associated with the pre-event column, post-event column and change column for respectively recording a pre-event measurement, a post-event measurement and a glucose change between the pre-event measurement and post-event measurement for each of a plurality of occurrences of a repeating event; and
    a unique details area adjacent the change column for recording unique details for each of the plurality of occurrences of the repeating event such that the unique details are correlated with the glucose change for each of the plurality of occurrences of the repeating event.

21. The glucose change evaluation chart of claim 20 wherein the glucose change evaluation chart is provided in a diabetes management package.

22. A method for displaying changes in glucose levels for a plurality of occurrences of a repeating event, the method comprising:
    receiving a selection of the repeating event from an input terminal;
    receiving, from the input terminal, a pre-event measurement, a post-event measurement, and unique details for each occurrence of the plurality of occurrences of the selected repeating event;
    determining, automatically with a processor, a glucose change between the pre-event measurement and post-event measurement for each occurrence of the plurality of occurrences of the selected repeating event; and
    displaying, on a display, the determined glucose change and the received unique details for each occurrence of the plurality of occurrences of the repeating event, such that the determined glucose change and the received unique details are visually correlated for each occurrence of the plurality of occurrences of the repeating event.

23. A method for displaying changes in glucose levels for a plurality of occurrences of a repeating event, the method comprising:

receiving a selection of the repeating event from an input terminal;

receiving, from the input terminal, a pre-event measurement, a post-event measurement and variations for each occurrence of the plurality of occurrences of the selected repeating event;

determining, automatically with a processor, a glucose change between the pre-event measurement and post-event measurement for each occurrence of the plurality of occurrences of the selected repeating event; and displaying, on a display, the determined glucose change and the received variations for each occurrence of the plurality of occurrences of the selected repeating event, such that the determined glucose change and the received variations are visually correlated for each occurrence of the plurality of occurrences of the repeating event.

* * * * *